(12) United States Patent
Yachia et al.

(10) Patent No.: US 8,696,736 B2
(45) Date of Patent: Apr. 15, 2014

(54) MEDICAL DEVICE HAVING AN UNRAVABLE PORTION

(75) Inventors: Daniel Yachia, Herzliya (IL); Ronnie Levy, Yigal (IL)

(73) Assignee: Allium Medical Solutions Ltd., Caesarea Industrial Park-South (IL)

( * ) Notice: Subject to any disclaimer, the term of this patent is extended or adjusted under 35 U.S.C. 154(b) by 114 days.

(21) Appl. No.: 10/515,057

(22) PCT Filed: May 23, 2003

(86) PCT No.: PCT/IL03/00427
§ 371 (c)(1),
(2), (4) Date: Feb. 17, 2005

(87) PCT Pub. No.: WO03/099166
PCT Pub. Date: Dec. 4, 2003

(65) Prior Publication Data
US 2005/0131423 A1    Jun. 16, 2005

(30) Foreign Application Priority Data
May 23, 2002   (IL) .......................................... 149829

(51) Int. Cl.
*A61F 2/88*    (2006.01)
(52) U.S. Cl.
USPC .......................... 623/1.22; 623/1.11; 623/1.15
(58) Field of Classification Search
USPC ................. 623/1.1, 1.11–1.54; 606/200, 194; 604/160, 164.05
See application file for complete search history.

(56) References Cited

U.S. PATENT DOCUMENTS

| | | | | |
|---|---|---|---|---|
| 3,993,078 A | * | 11/1976 | Bergentz et al. | 606/156 |
| 4,581,019 A | * | 4/1986 | Curelaru et al. | 604/164.05 |
| 4,790,809 A | * | 12/1988 | Kuntz | 604/8 |
| 5,037,427 A | | 8/1991 | Harada et al. | |
| 5,104,388 A | * | 4/1992 | Quackenbush | 604/264 |
| 5,226,913 A | * | 7/1993 | Pinchuk | 140/71 R |
| 5,281,204 A | * | 1/1994 | Horie et al. | 604/164.05 |
| 5,324,304 A | * | 6/1994 | Rasmussen | 606/200 |
| 5,443,496 A | * | 8/1995 | Schwartz et al. | 623/1.16 |
| 5,514,176 A | * | 5/1996 | Bosley, Jr. | 623/1.15 |
| 5,531,788 A | * | 7/1996 | Dibie et al. | 623/11.11 |
| 5,540,701 A | * | 7/1996 | Sharkey et al. | 606/153 |
| 5,716,410 A | * | 2/1998 | Wang et al. | 606/191 |

(Continued)

FOREIGN PATENT DOCUMENTS

| | | |
|---|---|---|
| EP | 1 110 561 A2 | 6/2001 |
| JP | 4-75668 A | 3/1992 |

(Continued)

OTHER PUBLICATIONS

European Office Action for corresponding European Application No. 03 723 039.8, dated May 12, 2010; seven pages.

*Primary Examiner* — Kathleen Holwerda
(74) *Attorney, Agent, or Firm* — Browdy and Neimark, PLLC

(57) ABSTRACT

A medical device, such as a stent, having a hollow portion formed from a fashioned filament (100, 110). Between adjacent segments of the fashioned filament is a detachable seam (140). After implantation of the device in the body, the device may subsequently be removed by grasping an end of the filament and pulling the end of the filament so as to detach the seam between adjacent segments of the fashioned filament, and unravel the hollow portion.

17 Claims, 7 Drawing Sheets

(56) References Cited

U.S. PATENT DOCUMENTS

| | | | |
|---|---|---|---|
| 5,772,668 A * | 6/1998 | Summers et al. | 623/1.11 |
| 5,902,334 A | 5/1999 | Dwyer et al. | |
| 5,928,261 A | 7/1999 | Ruiz | |
| 6,171,338 B1 * | 1/2001 | Talja et al. | 623/1.22 |
| 6,315,792 B1 * | 11/2001 | Armstrong et al. | 623/1.23 |
| 6,350,277 B1 * | 2/2002 | Kocur | 623/1.11 |
| 6,355,013 B1 * | 3/2002 | van Muiden | 604/96.01 |
| 6,361,558 B1 | 3/2002 | Hieshima et al. | |
| 6,364,904 B1 * | 4/2002 | Smith | 623/1.22 |
| 6,379,379 B1 * | 4/2002 | Wang | 623/1.15 |
| 6,790,226 B2 * | 9/2004 | Edwin et al. | 623/1.13 |
| 2002/0040236 A1 | 4/2002 | Lau et al. | |
| 2002/0052640 A1 | 5/2002 | Bigus et al. | |

FOREIGN PATENT DOCUMENTS

| | | |
|---|---|---|
| JP | 2001-526080 A | 12/2001 |
| WO | 9932051 A1 | 7/1999 |
| WO | 02/30329 A2 | 4/2002 |

\* cited by examiner

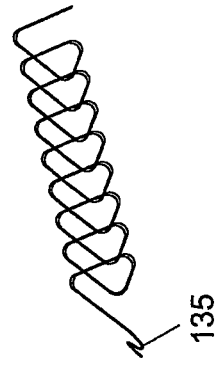
FIG. 1B
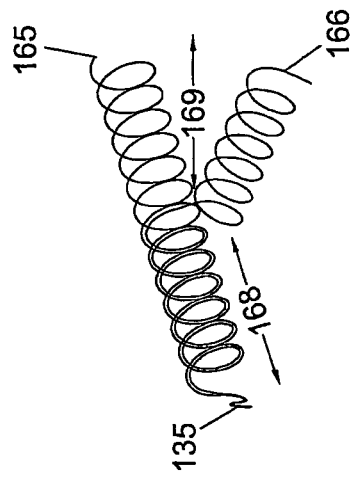
FIG. 1F
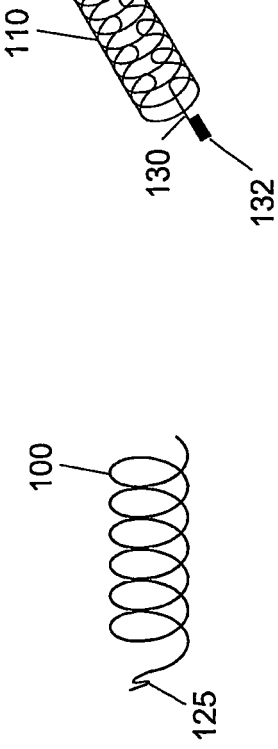
FIG. 1A
FIG. 1D
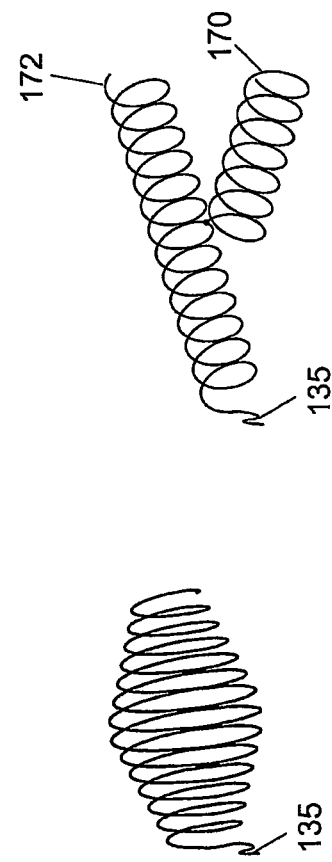
FIG. 1C
FIG. 1E

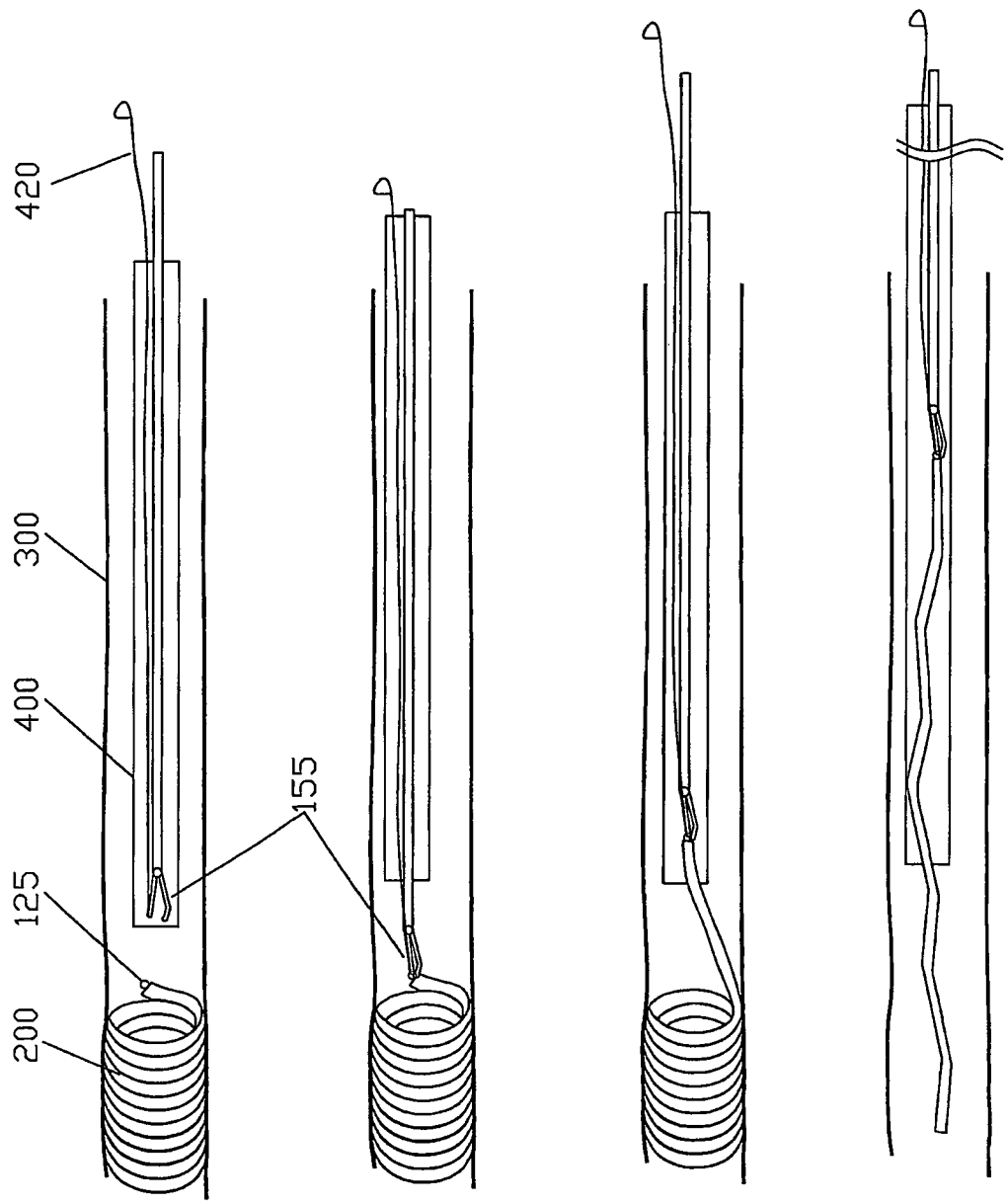

US 8,696,736 B2

MEDICAL DEVICE HAVING AN UNRAVABLE PORTION

FIELD OF THE INVENTION

This invention relates to medical devices, and more particularly to such devices having a hollow portion such as stents and catheters.

BACKGROUND OF THE INVENTION

Many indwelling medical devices have a hollow portion. For example, stents are hollow devices that are inserted into body ducts for preventing narrowing of the duct lumen, for tutoring a dilated lumen or for acting as a substrate for tissue growth. As another example, a catheter may have a hollow portion that may serve to transfer a fluid from outside the body to a body cavity, or for draining fluid from a body cavity. As yet another example, an artificial blood vessel valve has a casing enclosing a space through which blood flows.

The hollow portion of a medical device may have a fixed caliber in which it is both delivered and deployed. Alternatively, the hollow portion may be brought into an initial, small caliber, conformation in which it is inserted into the body and delivered to the site where it is to be deployed. This allows the hollow portion to be delivered with minimal damage to surrounding tissues. Deployment of the device involves expanding the hollow portion to a final larger caliber. When it is desired to remove the device from the body, the hollow portion may first be made to return to the small caliber conformation and then removed. For example, U.S. Pat. No. 5,037, 427 discloses a stent made from a two-way shape memory alloy. This stent has a transition temperature that is below body temperature in which it changes its diameter from a narrow diameter to a wide diameter. The stent is inserted into the body under a constant flow of cold fluid in order to maintain the stent in the narrow diameter during delivery. Once in the stent has been positioned in the desired location, the flow of the cold fluid is stopped and the stent then expands either spontaneously as it warms up to body temperature or by flowing a warm fluid around the stent. When the stent is to be removed, a flow of cold fluid is again applied to the stent causing the stent to soften and return to the narrow diameter conformation. The flow of cold fluid is maintained until the stent is removed from the body.

SUMMARY OF THE INVENTION

The present invention provides a medical device having a hollow portion such as a stent, catheter, filter or valve. In accordance with the invention, the hollow portion is formed from a flexible filament. The filament is fashioned into the shape of the hollow portion of the device. For example, if the hollow portion is a stent or the hollow shaft of a catheter, the filament may be fashioned into a helix. An end of the filament is configured so as to be graspable by a grasping device. Segments of the filament that are adjacent to each other after fashioning are attached to one another by means of a detachable seam. During delivery and deployment of the device, and while the device is in use, the seams are intact. When the device is to be removed from the body, the end of the filament is grasped by a grasping device, which may be located on the tip of a catheter or an endoscopic device. For example, the end of the filament may be from a magnetizable material, in which case the grasping device may consist of a magnet. Alternatively, a hook may be present at an end of the filament, in which case, the grasping device contains a hook capable of engaging the hook on the filament. The grasping device is withdrawn from the body, pulling the grasped end of the filament along with it. As the grasping device continues to be withdrawn, the continued pulling on the grasped end of the filament causes the seams in the device to split. As the filament continues to be pulled, the hollow portion of the device progressively unravels until the filament becomes essentially linear and is easily removed from the body.

In its first aspect, the invention thus provides a medical device having at least a hollow portion, the hollow portion being formed from a fashioned filament and having a detachable seam between at least one pair of adjacent segments of the fashioned filament.

In its second aspect, the invention provides a method for removing a hollow portion of a medical device from a body, the hollow portion being formed from a fashioned filament and having a detachable seam between adjacent segments of the fashioned filament, comprising:
  (a) Grasping an end of the filament;
  (b) pulling the end of the filament so as to detach the seam between adjacent segments of the fashioned filament.

In its third aspect, the invention provides a method for forming a hollow portion of a medical device, the hollow portion having a shape comprising the method:
  (a) forming a filament into the shape of the device;
  (b) forming a seam between at least one pair of adjacent segments of the fashioned filament.

BRIEF DESCRIPTION OF THE DRAWINGS

In order to understand the invention and to see how it may be carried out in practice, a preferred embodiment will now be described, by way of non-limiting example only, with reference to the accompanying drawings, in which:

FIGS. 1A-1F show formation of a filament for use in the construction of a hollow tubular portion of a medical device in accordance with the invention;

FIGS. 5A-5D show removal of the device of FIG. 4 from the body;

DETAILED DESCRIPTION OF THE INVENTION

First Embodiment

Figure 2C:
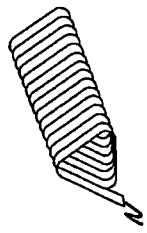
FIGS. 2A-2F show the filaments of FIG. 1 after application of a coating.
Figure 2B:
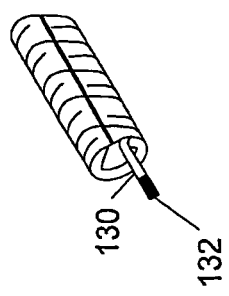
Figure 2A:
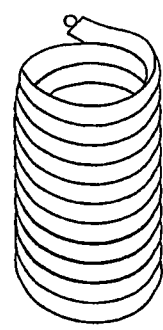
Figure 2F:
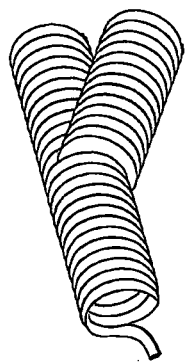
Figure 2E:
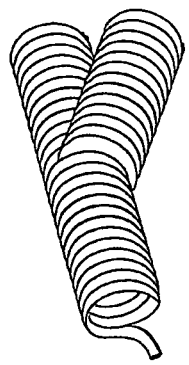
Figure 2D:
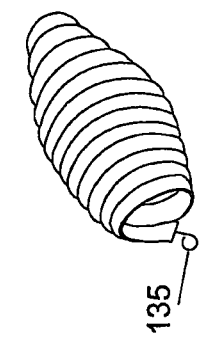

FIG. 1 shows the construction of a hollow portion of a medical device in accordance with the invention. In FIGS. 1*a*, *b*, and *c*, a flexible filament is fashioned into a desired shape. The filament may be for example a metal wire from stainless steel or a nickel-titanium alloy (Nitinol). In FIG. 1*a*, the filament 100 has been fashioned into a helix that may be used as a cylindrical hollow portion of a stent, or catheter, or artificial blood vessel valve. FIG. 1b shows an alternative method for fashioning a filament 110 into an essentially cylindrical form that may be used in a stent or catheter. The cylinders shown in FIGS. 1a and 1b have a circular cross-section. This is by way of example only, and the filament may be fashioned into a cylinder having any desired cross-sectional shape as required by any particular application. A filament that has been fashioned into a cylinder having a triangular cross-section, as shown in FIG. 1c, or an hourglass cross-section may be used in the construction of a stent for insertion into a tubular body organ having a triangular cross-section or an hourglass cross-section, such as the prostatic urethra. A filament that has been fashioned into a cylinder having a variable diameter, as shown in FIG. 1d, may be used in the construction of an artificial blood vessel valve or filter. Two sub-filaments may joined to form a bifurcating filament, as shown in FIGS. 1e and 1f, that may be used in the construction of a bifurcating stent to be used at a bifurcation in a blood vessel. In FIG. 1e, an end of a sub-filament 170 is attached at the middle of a sub-filament 172. The attachment may be formed, for example, by welding of the two sub-filaments together at the point of attachment. Alternatively, the attachment of the two sub-filaments may be maintained by a coating of the filament, as described in detail below. In FIG. 1f, two sub-filaments 165 and 166 are fashioned parallel to each other in a non-bifurcated portion 168 of the filament. In the bifurcated portion 169 of the filament, the two sub-filaments separate and are fashioned individually. The shapes and applications shown in FIG. 1 are by way of example only, and the invention provides implantable medical devices having a hollow portion of any shape and dimensions as required in any particular application.

Figure 8:
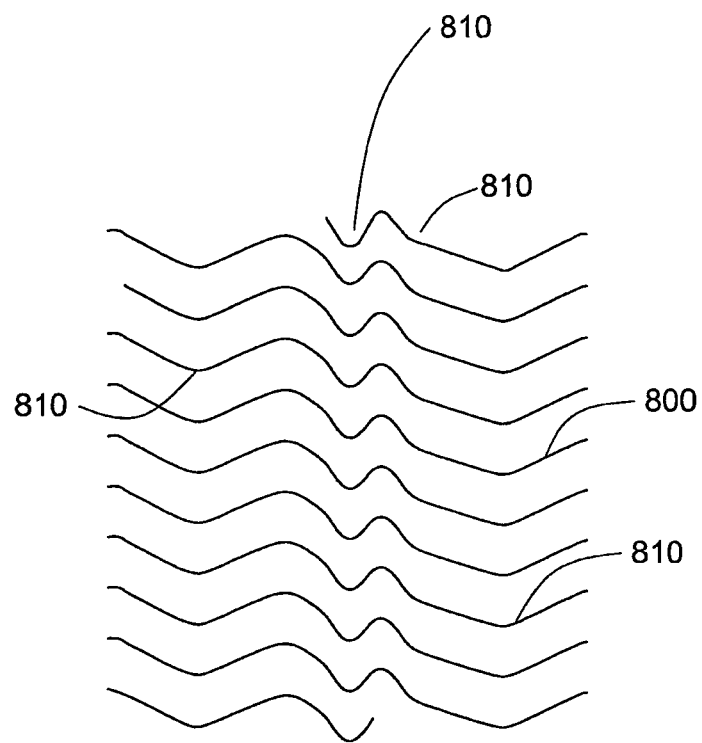
FIG. 8 shows schematically a filament fashioned into a helix having a triangular cross-section with bends along its length.

One or more bends may be introduced in the filament in order to facilitate folding of the tubular portion, as described below. FIG. 8 shows, for example, a filament 800 folded into a cylinder having a triangular cross-section having folds 810 periodically arranged along its length. For clarity, the cylinder in FIG. 8 is represented as having been sectioned longitudinally and unrolled onto the plane of the Figure.

After fashioning into the desired shape, an end of the filament is configured to be graspable by a grasping device as explained below. In FIG. 1a, for example, an end 125 has been fashioned into a planar shape that is graspable by a spring biased clamp located on a grasping device. As another example, in FIG. 1b, and end 130 has a magnetizable portion 132 that may engage a magnetizable portion on a grasping device. As yet another example, in FIGS. 1c to 1f, an end 135 of the filament 120 has been fashioned into a hook that may engage a hook on a grasping device.

Once the filament has been fashioned into the desired shape, a polymer suspension is applied to the filament so as to form a thin coating on the filament. The polymer suspension is applied by any known method such as brushing, spraying or immersion of the filament. After applying the polymer solution, the solution is allowed to cure on the filament. FIGS. 2a to 2f show the filaments of FIGS. 1a to 1f, respectively, after application of the polymer suspension. The cured polymer fills in spaces between adjacent regions of the fashioned filament so as to provide the coated filament with a continuous surface.

Figure 3:
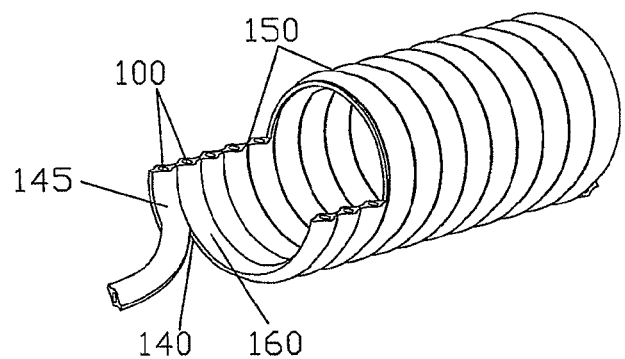
FIG. 3 shows seams in a hollow portion of an implantable device of the invention.

FIG. 3 shows, as an example, the filament 100 after application of the polymer solution to produce the hollow portion 160 of an implantable medical device. For better clarity, part of the filament and associated coating has been cut out. The polymer has formed a continuous coating 150 on the filament 100. The polymer has thus formed seams between regions of the fashioned filament 100 that are adjacent to one another, for example the seam 140 between the regions 145 and 160 of the filament 100. The polymer coating 150 is selected so that the seams 140 are torn when adjacent regions in the fashioned filament joined by a seam are separated, as explained in detail below. The seam may be weakened to facilitate removal, as described below, by making the thickness of the coating thinner in the seams than it is along the filament or by perforations (not shown) introduced into the seam. The polymer solution may optionally be chosen so that the coated filament is elastic. The polymer solution may be for example a 2:3 solution of silicone rubber and a solvent. This solution may be used when it is desired that the hollow portion be elastic. In this case, the hollow portion may be deformed into a small caliber conformation and maintained in this conformation, for example, by a constraining sleeve. After positioning of the device in the body, the device is deployed by removing the constraint. Due to the elasticity of the hollow portion, the hollow portion then returns to its undeformed conformation.

Figure 4:
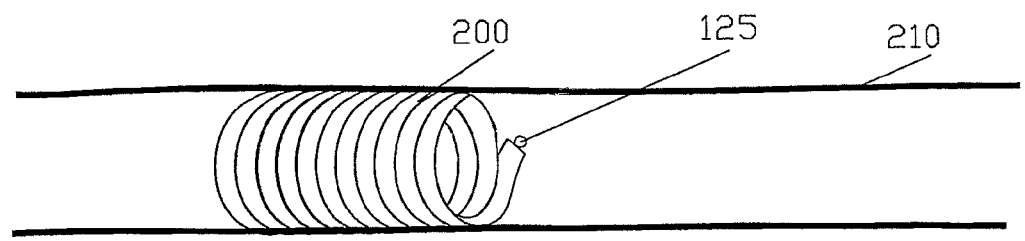
FIG. 4 shows a hollow portion of a device of the invention after insertion into the body.

FIG. 4 shows a device comprising the hollow portion 200 of a medical device formed as above, after deployment in the body. The device may be, for example, a stent, catheter, filter or valve that has been introduced into a body duct 210, such as a blood vessel.

FIG. 5 shows removal of the hollow portion 200 from the body. In FIG. 5a, a retriever 400 is inserted into the body. At the distal end of the catheter is a grasping device 155 configured to engage the end 125 of the filament 100. In the example shown in FIG. 5, the end 125 has been fashioned into a planar region, and the grasping device 155 is a spring biased clamp that is configured to grasp the planar region. The spring biased closed 155 clamp is opened by pulling a wire 420 that extends from the clamp 155 to the proximal end 430 of the retriever 400.

Once the end 125 has been engaged by the grasping means of the retriever 400, the retriever is withdrawn from the body duct 300, and the end is pulled away from the device. Since the device is lodged in the body duct, as the retriever 400 is withdrawn and the end is pulled, the seam between adjacent regions of the filament tears, and the coated filament progressively unravels (FIG. 5c). The tearing is facilitated if the polymer coating in the seam is weaker than in regions adjacent to the filament, for example, by scoring the coating along the seam to make the seam thinner than the rest of the coating, or by introducing perforations in the coating along the seam. The filament continues to unravel until the stent is essentially linear (FIG. 5d) and can be removed from the body. In the case of the bifurcated device shown in FIG. 2e, as the filament unravels, it assumes a bifurcated or Y shape that is easily removed from the body. In the case of the bifurcated device shown in FIG. 2f, in which the attachment of the two sub-filaments is maintained by the polymer coating, one of the two sub-filaments is first removed causing the polymer coating at the attachment to tear so as to separate the two sub-filaments. The second sub-filament is then removed.

Second Embodiment

Figure 6A:
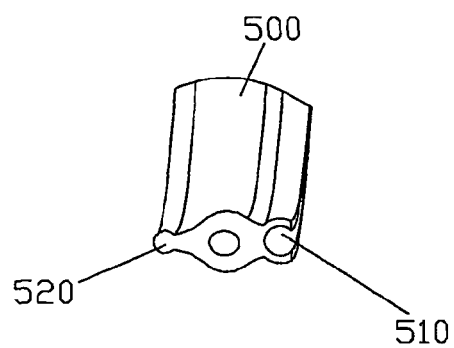
FIGS. 6A-6C show formation of a hollow tubular portion of a medical device in accordance with another embodiment of the invention
Figure 6B:
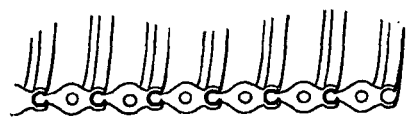
Figure 6C:
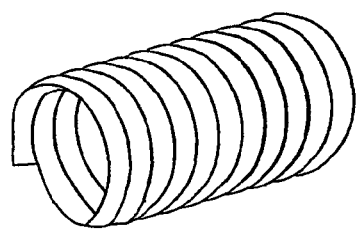

FIG. 6 shows the construction of a hollow portion of an implantable medical device in accordance with a second embodiment of the invention. As shown in FIG. 6a, a filament 500 is used having a groove 510 extending longitudinally along one edge of the filament and a ridge 520 also extending longitudinally along the filament. The filament is made from a resiliently flexible material such as rubber. The groove 510 and the ridge 520 are positioned diametrically opposite one another on the filament. The groove 510 and the ridge 520 are shaped so that the ridge 520 on one segment of the filament may be snapped into the groove on another segment of the filament as shown in FIG. 6*b*. The filament is brought into a desired configuration, for example a helix as shown in FIG. 6*c*. The ridge 520 of the filament in each turn of the helix is snapped into the groove 510 on an adjacent turn of the helix, to produce a detachable seam along the length of the filament. This device may be inserted into the body and removed as explained for the previous embodiment.

Third Embodiment

Figure 7:
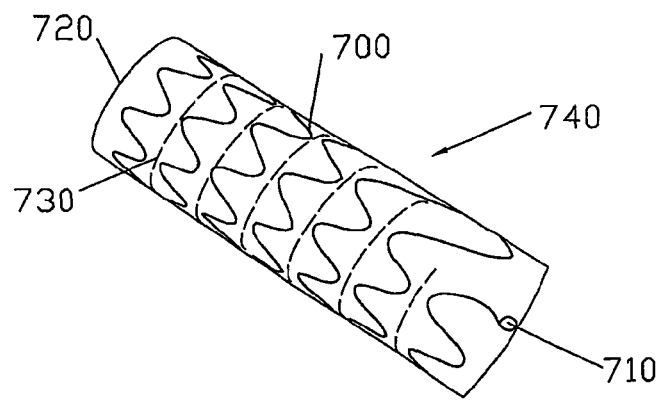
FIG. 7 shows another embodiment of the invention having a filament fashioned into an undulating helix embedded in a polymeric coat.

FIG. 7 shows another embodiment 740 of the invention in which a filament 700 has been fashioned into an undulating helix. A removal hook 710 has been formed at an end of the filament 700. The filament 700 is contained in a polymeric layer 720 such as polyurethane, silicone rubber, or a copolymer of polyurethane and silicon. The polymeric layer 720 can be made by a dipping process, or by molding extrusion. The polymeric coating 720 is weakened between adjacent turns of the helix (along the curve 730) in order to facilitate removal as described above for the other embodiments. After the device 740 is deployed in the body, it may be removed by pulling on the removal hook 710, as explained above in reference to FIG. 5. In this case, the polymeric coating forms a strip containing the undulating helical filament 720.

Figure 9A:
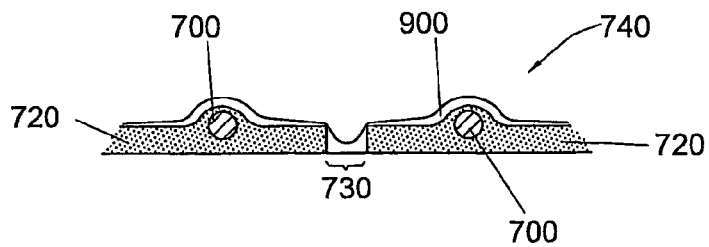
FIGS. 9A-9F show weakening of the polymeric coat between turns of the helix of the embodiment of FIG. 7.
Figure 9B:
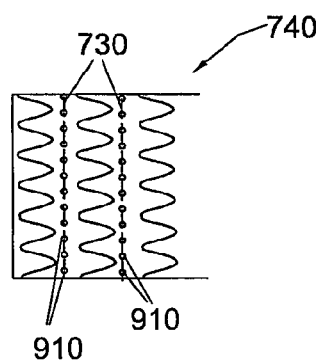
Figure 9C:
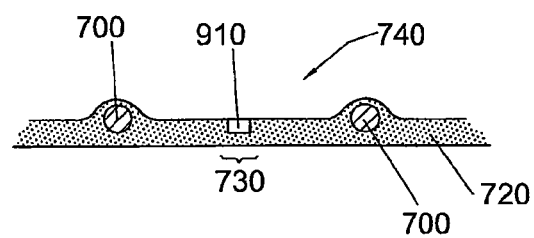
Figure 9D:
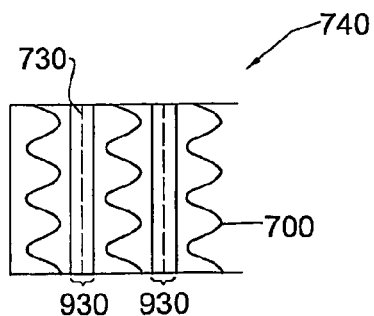
Figure 9E:
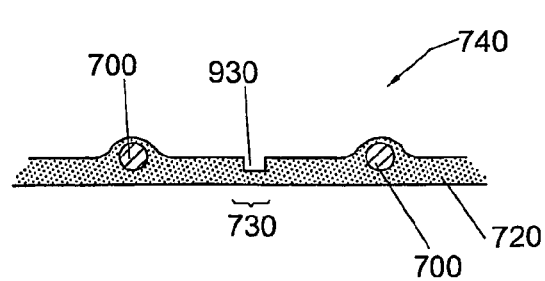
Figure 9F:
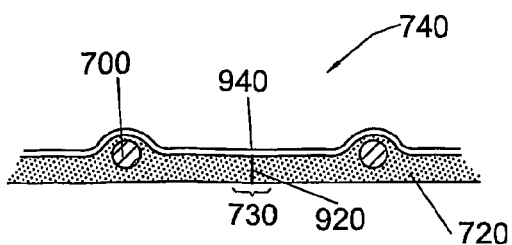

Any method may be used to achieve weakening of the polymeric coating along the curve 730. For example, as shown in FIG. 9*a*, a narrow helical strip is cut out of the polymeric material 720 along the curve 730, and a weaker external polymeric coat 900 is applied to the device 740 that also replaces the removed material. FIGS. 9*b* and 9*c* show weakening the polymeric coat 720 by introducing perforations 910 along the curve 730. The perforations are shown en face in FIG. 9*b* and in cross-section in FIG. 9*c*. The perforations 910 may be blind perforations formed as shown in FIG. 9*c*, or may extend through the entire thickness of the polymeric layer 720. FIGS. 9*d* and 9*e* show another method for weakening the polymeric coat 720 in which a groove 930 is routed in the polymeric coat 720 along the curve 730. The groove 910 is shown en face in FIG. 9*d* and in cross-section in FIG. 9*e*. FIG. 9*f* shows yet another method for weakening the polymeric coat 720 in which a cut 920 is made along the curve 730 without removing any of the polymeric material 720, and a weaker external polymeric coat 940 is applied to the device 740.

The invention claimed is:

1. A medical device comprising a stent, the stent comprising:
   a tubular polymeric layer having an undulating filament contained therein, which undulating filament is fashioned into a helix, wherein said tubular polymeric layer comprises at least one seam thereon, the seam being located between at least one pair of adjacent turns of the helix of undulating filament, said seam being one or more of a groove, an empty strip, a slit, and a perforation, thereby providing a weakened wall portion in the tubular polymeric layer; and
   a coating having a strength that is weaker than the strength of the tubular polymeric layer, the coating sealing the one or more of the groove, the empty strip, the slit, and the perforation, thereby providing the stent with a weakened impermeable seam in the tubular polymeric layer, between the adjacent turns of the helix of undulating filament, whereby the impermeable seam separates apart upon pulling an end of the undulating filament away from the stent, and when the end of the undulating filament contained in the tubular polymeric layer is pulled sufficient to remove the medical device, the stent is removed as a strip of the polymeric layer containing the undulating filament,
   wherein the tubular polymeric layer has a thickness in a portion of the seam that is less than the thickness of the tubular polymeric layer surrounding the undulating filament adjacent to the seam.

2. The medical device according to claim 1, further comprising a hook, wherein the hook is provided at the end of the undulating filament.

3. The medical device according to claim 1, further comprising a magnetizable portion provided at the end of the undulating filament.

4. The medical device according to claim 1, wherein the stent has a circular, triangular or hourglass cross-section.

5. The medical device according to claim 1, wherein the seam is a single continuous seam.

6. A method for producing a medical device comprising a stent, in accordance with claim 1, comprising:
   making an undulating filament that is fashioned into a helix;
   causing the helical undulating filament to become contained in a layer of polymeric material to form a tubular polymeric layer having the helical undulating filament contained therein;
   forming a seam in the tubular polymeric layer, the seam being located between at least one pair of adjacent turns of the helix of undulating filament, the seam being one or more of a groove, an empty strip, a slit and a perforation, thereby providing a weakened wall portion in the tubular polymeric layer; and
   coating the tubular polymeric layer with a coating material having a strength that is weaker than the strength of the tubular polymeric layer, wherein the coating seals the one or more of the groove, the empty strip, the slit, and the perforation, thereby providing a stent with a weakened impermeable seam in the tubular polymeric layer, between the adjacent turns of the helix of undulating filament, wherein the tubular polymeric layer has a thickness in a portion of the seam that is less than the thickness of the tubular polymeric layer surrounding the undulating filament adjacent to the seam.

7. A system comprising:
   a medical device comprising a stent, the stent comprising
      a tubular polymeric layer having an undulating filament contained therein, which undulating filament is fashioned into a helix, wherein said tubular polymeric layer comprises at least one seam thereon, the seam being located between at least one pair of adjacent turns of the helix of undulating filament, said seam being one or more of an empty strip, a slit, and a perforation, thereby providing a weakened wall portion in the tubular polymeric layer; and
      a coating having a strength that is weaker than the strength of the tubular polymeric layer, the coating sealing the one or more of the empty strip, the slit, and the perforation in said tubular polymeric layer, thereby providing the stent with a weakened impermeable seam in the tubular polymeric layer, between the adjacent turns of the helix of undulating filament, whereby the impermeable seam separates apart upon pulling an end of the undulating filament away from the stent, and when the end of the undulating filament contained in the tubular polymeric layer is pulled sufficient to remove the medical device, the stent is removed as a strip of the polymeric layer containing the undulating filament; and a grasping device configured so as to grasp an end of the undulating filament.

8. The system according to claim 7, wherein, in said medical device, said seam is a perforation.

9. The system according to claim 7, wherein, in the medical device, the tubular polymeric layer has a thickness in a portion of the seam that is less than the thickness of the tubular polymeric layer surrounding the undulating filament adjacent to the seam.

10. The system according to claim 7, wherein the medical device further comprises a magnetizable portion provided at the end of the undulating filament and the grasping device further comprises a magnetizable portion.

11. The system according to claim 7, wherein the medical device further comprises a hook provided at the end of the undulating filament and the grasping device further comprises a hook.

12. The system according to claim 7, wherein said grasping device is a spring biased clamp configured sufficient to grasp the end of the undulating filament.

13. The medical device according to claim 7, wherein, in said medical device, said seam is a slit through the tubular polymeric layer.

14. The medical device according to claim 7, wherein, in said medical device, said seam is an empty strip through the tubular polymeric layer.

15. A medical device comprising a stent, the stent comprising:

a tubular polymeric layer having an undulating filament contained therein, which undulating filament is fashioned into a helix, wherein said tubular polymeric layer comprises at least one seam thereon, the seam being located between at least one pair of adjacent turns of the helix of undulating filament, said seam being a perforation, thereby providing a weakened wall portion in the tubular polymeric layer; and a coating having a strength that is weaker than the strength of the tubular polymeric layer, the coating sealing the perforation, thereby providing the stent with a weakened impermeable seam in the tubular polymeric layer, between the adjacent turns of the helix of undulating filament, whereby the impermeable seam separates apart upon pulling an end of the undulating filament away from the stent, and when the end of the undulating filament contained in the tubular polymeric layer is pulled sufficient to remove the medical device, the stent is removed as a strip of the polymeric layer containing the undulating filament.

16. A medical device comprising a stent, the stent comprising:

a tubular polymeric layer having an undulating filament contained therein, which undulating filament is fashioned into a helix, wherein said tubular polymeric layer comprises at least one seam thereon, the seam being located between at least one pair of adjacent turns of the helix of undulating filament, said seam being a slit through the tubular polymeric layer, thereby providing a weakened wall portion in the tubular polymeric layer; and a coating having a strength that is weaker than the strength of the tubular polymeric layer, the coating sealing the slit, thereby providing the stent with a weakened impermeable seam in the tubular polymeric layer, between the adjacent turns of the helix of undulating filament, whereby the impermeable seam separates apart upon pulling an end of the undulating filament away from the stent, and when the end of the undulating filament contained in the tubular polymeric layer is pulled sufficient to remove the medical device, the stent is removed as a strip of the polymeric layer containing the undulating filament.

17. A medical device comprising a stent, the stent comprising:

a tubular polymeric layer having an undulating filament contained therein, which undulating filament is fashioned into a helix, wherein said tubular polymeric layer comprises at least one seam thereon, the seam being located between at least one pair of adjacent turns of the helix of undulating filament, said seam being an empty strip through the tubular polymeric layer, thereby providing a weakened wall portion in the tubular polymeric layer; and a coating having a strength that is weaker than the strength of the tubular polymeric layer, the coating sealing the empty strip, thereby providing the stent with a weakened impermeable seam in the tubular polymeric layer, between the adjacent turns of the helix of undulating filament, whereby the impermeable seam separates apart upon pulling an end of the undulating filament away from the stent, and when the end of the undulating filament contained in the tubular polymeric layer is pulled sufficient to remove the medical device, the stent is removed as a strip of the polymeric layer containing the undulating filament.

* * * * *